United States Patent
Wang et al.

(10) Patent No.: US 8,791,156 B2
(45) Date of Patent: Jul. 29, 2014

(54) POLYACETYLENE COMPOUND, AN EXTRACT CONTAINING THE SAME AND APPLICATION THEREOF

(76) Inventors: Sheng-Yang Wang, New Taipei (TW); Ting-Yu Lin, Taichung (TW); Chieh-Yin Chen, Taichung (TW); Shih-Chang Chien, Taichung (TW); Wen-Wei Hsiao, Taipei (TW); Fang-Hua Chu, Taipei (TW); Wen-Hsiung Li, Taipei (TW); Jei-Fu Shaw, Kaohsiung (TW); Chin-Chung Lin, Taipei (TW)

( * ) Notice: Subject to any disclaimer, the term of this patent is extended or adjusted under 35 U.S.C. 154(b) by 116 days.

(21) Appl. No.: 13/323,057

(22) Filed: Dec. 12, 2011

(65) Prior Publication Data

US 2013/0150436 A1 Jun. 13, 2013

(51) Int. Cl.
*A61K 31/36* (2006.01)
*C07D 317/64* (2006.01)

(52) U.S. Cl.
CPC .............. *A61K 31/36* (2013.01); *C07D 317/64* (2013.01)
USPC .......................................... 514/464; 549/445

(58) Field of Classification Search
CPC ...................................................... C07D 317/64
USPC .......................................... 514/464; 549/445
See application file for complete search history.

(56) References Cited

PUBLICATIONS

Ting-Yu Lin et al., "Metabolite Profiles for *Antrodia cinnamomea* Fruiting Bodies Harvested at Different Culture Ages and from Different Wood Substrates," Journal of Agricultural and Food Chemistry, Jun. 9, 2011 vol. 59(14), pp. 7626-7635.

*Primary Examiner* — Taofiq A Solola

(57) ABSTRACT

A polyacetylenes and application thereof. The polyacetylenes is isolated from an extract of the sporophores of *Antrodia Cinnamomea* and has a function of inhibiting the production of nitric oxide. Therefore, the polyacetylenes can be used for preparing a pharmaceutical composition for anti-inflammation. The present invention also teaches the representative metabolites of the sporophores of *Antrodia Cinnamomea*, which can be used to evaluate the quality thereof.

13 Claims, 3 Drawing Sheets

POLYACETYLENE COMPOUND, AN EXTRACT CONTAINING THE SAME AND APPLICATION THEREOF

BACKGROUND OF INVENTION

1. Field of the Invention

The present invention relates generally to polyacetylenes and its application, and more particularly to polyacetylenes extracted from *Antrodia Cinnamomea* and application thereof.

2. Description of Related Art

*Antrodia Cinnamomea* (also called *Antrodia Camphorata*), is a perennial fungus belonging to Aphyllophorales, Polyporaceae, and is only found in Taiwan. *Antrodia Cinnamomea* can only parasitize on the inner wall of the decayed and hollow core of *Cinnamoum Kanehirai Hay*. Because *Cinnamoum Kanehirai* is a rare and preserved kind of tree in Taiwan, and the growth of *Antrodia Cinnamomea* is very slow, *Antrodia Cinnamomea* is also very rare. Although under the drive of market demand, researches have overcome the limitation that *Antrodia Cinnamomea* can only parasitize on *Cinnamoum Kanehirai Hay*, the price of *Antrodia Cinnamomea* is still very high because of its outstanding medicinal value.

According to traditional Taiwanese medicine, *Antrodia Cinnamomea* has the potential to cure hepatopathy, hypertension, abdominalgia and cancer. The scientific community is also greatly interested in the complex ingredients contained in *Antrodia Cinnamomea*. Currently known physiologically active ingredients contained in *Antrodia Cinnamomea* include: triterpenoids, polysaccharides (like β-D-dextran), adenosine, vitamin (like vitamin B and niacin), SOD (superoxide dismutase), nucleic acid, steroid and blood pressure stabilizing agents (like antodia acid) etc. Particularly, most studies are on triterpenoids. However, although there are more and more studies focusing on development of the ingredients of *Antrodia Cinnamomea* having medicinal values, currently there is still no complete establishment on the metabolism of *Antrodia Cinnamomea* during its growing and maturing processes.

Generally, the sporophores of *Antrodia Cinnamomea* are regarded as the part with most medicinal value, but there is still no complete experimental method to study the physical components of the sporophores of *Antrodia Cinnamomea*. In order to properly use *Antrodia Cinnamomea* in the preparation of medicines, a complete analysis of the physical components of the sporophores of *Antrodia Cinnamomea* will provide a thorough and good understanding of various compounds contained in *Antrodia Cinnamomea*, and the unique therapeutic effectiveness and use of each compound.

SUMMARY OF THE INVENTION

Although many compounds contained in *Antrodia Cinnamomea* has been confirmed through experiments, there is still no establishment of a complete experimental method to study the physical components of the sporophores of *Antrodia Cinnamomea*. Through an analysis on the physical components of the sporophores of *Antrodia Cinnamomea*, the present invention confirmed a representative physical metabolite, and consequently established a method to evaluate the quality of *Antrodia Cinnamomea*. In the above-mentioned representative physical metabolite, the present invention further discovered a new compound and examined its potential medicinal value.

The polyacetylenes of the present invention has a structural formula as disclosed in the following Formula (I):

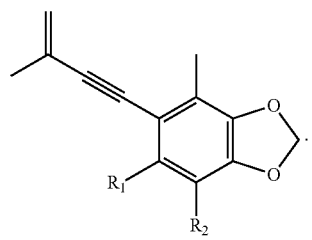

The above R1 and R2 is identical or different alkoxy; and preferably alkoxy of C1~C4.

The *Antrodia Cinnamomea* extract disclosed in the present invention explicitly refers to extract from the sporophores of *Antrodia Cinnamomea*. The *Antrodia Cinnamomea* extraction method disclosed in the present invention can be summarized as follow: Firstly, mix the dry sporophores of *Antrodia Cinnamomea* with alcohol thoroughly, and then extract for 60~120 min. There is no specific limitation on the mixing method, for example, an ultrasonic vibrator can be used to enhance mixing efficiency. Then, the obtained crude extract is dried and re-dissolved in methyl. At last, the extract from sporophores of *Antrodia Cinnamomea* can be obtained by passing the methyl containing the above crude extract through an SPE cartridge (Sep-Pak C18, Water Co., Milford, Mass. USA).

"Medical acceptability" mentioned in the present invention means no influence on the normal physical reactions of the tested individual during the clinical trial, and particularly no bad reactions with the carried active ingredients. Said bad reactions include reduction or disappearance of effectiveness of the above active ingredients, or interaction with the above active ingredients to produce substance harmful to the given individual.

"Medically acceptable carriers" mentioned in the present invention include but not limited to: lactose, starch, cellulose derivatives, magnesium stearate, steric acid, water, appropriate oils, normal saline solution, water solution of dextrose or any combination of the above. The pharmaceutical composition of the present invention can be in various dosage forms: capsule, pastille, dispersant, liquid, suspension or injection. More specifically, appropriate medically acceptable carriers can be chosen based on the form of the pharmaceutical composition of the present invention. For example, in the form of capsules, usually adopted carriers include: lactose, starch, cellulose derivatives, magnesium stearate, steric acid or any combination of the above.

Preferably, the pharmaceutical composition of the present invention contains 5~95 wt % active ingredients; and 5~95 wt % medically acceptable carrier. The above active ingredients include the polyacetylenes of the present invention or *Antrodia Cinnamomea* extract containing the above polyacetylenes. Depending upon circumstances, the pharmaceutical composition of the present invention can be added with medically acceptable stabilizers, preservatives, antioxidants, or any combination of the above. Those of ordinary skill in the art shall easily understand that, the dosages of the pharmaceutical composition of the present invention can be changed depending on various factors, for example, appropriate adjustments can be made depending on administration mode and means, age, health and weight of the acceptor, nature and degree of the diagnosis, type of parallel treatment, frequency of treatment and expected effect.

"Quality" mentioned in the present invention means the degree of maturation of the *Antrodia Cinnamomea*, and the content of ingredients with medicinal value. Said degree of maturation means the *Antrodia Cinnamomea* unit is in such a state: sufficient ingredients of medicinal value have been produced, and the content of such ingredients in the unit is stable. "Evaluation of the quality of the *Antrodia Cinnamomea*" mentioned in the present invention means measuring the state of the *Antrodia Cinnamomea* obtained, or measuring the state of the sporophores of *Antrodia Cinnamomea* or extract of the sporophores of *Antrodia Cinnamomea* obtained, or the state of the *Antrodia Cinnamomea* as the source of the above sporophores.

Embodiment I: The *Antrodia Cinnamomea* Used by the Present Invention

The *Antrodia Cinnamomea* used by the present invention is obtained by National Chung Hsing University. Totally four strains are obtained: AC-3, AC-5, AC-7 and AC-9. For the purpose of experiment, the four strains are cultured on *Cinnamoum Kanehirai* for 9 months to obtain four strains of AC-3-9, AC-5-9, AC-7-9 and AC-9-9; apart from the strain cultured for 9 months, AC-9 is also cultured for 3 months, 6 months and 12 months to obtain: AC-9-3, AC-9-6, AC-9-12.

Embodiment II: Obtain Extract of the Sporophores of *Antrodia Cinnamomea*

Before proceeding to the extracting steps, the efficiency of each extraction time is tested to optimize the extracting effect. To test the optimal extraction time, dry the fresh sporophores of *Antrodia Cinnamomea* for 72 hours, and crush them into powder with average granule size less than 0.7 mm. Measure 5 g of the sporophore powder, and put it into a flask of 250 mL to mix with 100 mL of alcohol (EtOH). Put the flask filled with sporophore powder and alcohol in an ultrasonic vibrator (Branson 5510, Branson Ultrasonic, Ontario, Canada) for thorough mixing. Mix the sporophore powder and alcohol for respectively 10, 20, 30, 60, 120 minutes (extraction time), decant and filter them in vacuum. Then, concentrate and dry them in a rotary evaporator. The yields obtained from each extraction time are listed in the following Table 1, wherein the data shown are presented as average value±standard error (n=3).

TABLE 1

Extraction time and yield

| Extraction time (min) | Yield (%) |
|---|---|
| 10 | 27.75 ± 2.95$^a$ |
| 20 | 28.25 ± 1.41$^a$ |
| 30 | 28.84 ± 1.36$^a$ |
| 60 | 31.34 ± 2.19$^b$ |
| 120 | 31.91 ± 4.16$^b$ |

Data marked with "a" and data marked with "b" has statistical difference.

It is known from the data in Table 1 that, the yields basically increase along with increase of the extraction time, and are reflected in two groups: 10, 20, and 30 versus 60 and 120. Considering yield and time efficiency, the present invention adopted 60 min as the optimal extraction time.

After determining the optimal extraction time, conduct extraction to obtain the *Antrodia Cinnamomea* extract needed by the present invention. Firstly, obtain dry sporophores of the *Antrodia Cinnamomea* strains mentioned in Embodiment I. Under normal atmospheric temperatures, extract 580 g of sporophores of *Antrodia Cinnamomea* with 95% alcohol. Dry the alcohol crude extract obtained under vacuum, and obtain 183.9 g of dry product. Then dissolve the dry product in methyl (10 mg/mL), and pass the solution through a SPE cartridge (Sep-Pak C18, Water Co., Milford, Mass. USA) to obtain *Antrodia Cinnamomea* sporophore extract of this embodiment.

Embodiment III: Analyze the Composition of *Antrodia Cinnamomea* AC-9-9 Extract Obtained in Embodiment II To thoroughly understand the ingredients contained in the *Antrodia Cinnamomea* sporophore extract, this embodiment uses HPLC method to further isolate the extract obtained in Embodiment I.

The HPLC method adopted by this embodiment uses Agilent 1100 HPLC system with UV detector. The fixed phase is Luna C18 column (250×10.0 mm, Phenomenex, Torrance Calif.). The mobile phase is a mixture of the following three solutions: (A)water; (B)methyl (MeOH); (C)acetonitrile. Gradient elution profile is as follows: 0~5 min, A:B:C=40:30:30 (isocratic); 5~95 min, A:B:C=40:30:30 to A:B:C=10:10:80 (linear gradient); 95~105 min, A:B:C=10:10:80 to A:B:C=0:0:100 (linear gradient); 105~115 min, 100% C (isocratic). Flow rate at 0~95 min is 0.5 mL/min, at 95~115 min is 1.0 mL/min. Detecting wave length is 254 nm.

From the extract of Embodiment I, 13 compounds are isolated, with their retention time respectively being: 17.9 min (compound a); 20.8 min (compound b); 38.1 min (compound c); 41.2 min (compound d); 42.1 min (compound e); 46.1 min (compound f), 48.7 min (compound g); 51.8 min (compound h); 53.4 min (compound i); 55.0 min (compound j); 67.8 min (compound k); 73.2 min (compound l); 102.7 min (compound m). Through optical spectrum analysis, compounds a-m are further identified, as shown in the following Table 2:

TABLE 2 compounds a~m

| Compound a | (R,S)-Antrodia Cinnamomea Acid K (Antcin K) |
|---|---|
| Compound b | 1,4-dimethoxy-2,3-methylenedioxy-5-methylbenzene |
| Compound c | (R,S)-Antrodia Cinnamomea Acid C (Antcin C) |
| Compound d | Antrocamphin A (Antrocamphin A) |
| Compound e | 2,2'5,5'-tetramethoxy-3,4,3',4'-bimethylenedioxy-6,6'-dimethylbiphenyl (2,2',5,5'-tetramethoxy-3,4,3',4'-bimethylenedioxy-6,6'-dimethylbiphenyl) |
| Compound f | (R,S)-Antrodia Cinnamomea Acid H (Antcin H) |
| Compound g | Dehydrosulfurenic acid |
| Compound h | Antrocamphin C (new compound) |
| Compound i | (R,S)-Antrodia Cinnamomea Acid B (Antcin B) |
| Compound j | (R,S)-Antrodia Cinnamomea Acid G (Antcin G) |
| Compound k | (R,S)-Antrodia Cinnamomea Acid A (Antcin A) |
| Compound l | 15-Acetyl-dehydrosulphurenic acid |
| Compound m | Dehydroeburicoic acid |

From the above Table 2, it is known that compounds a, c, f, g, i, j, k, l, m are triterpenoids and steroids; compound d and h are polyacetylenes; compound b and e are benzenoids. It is to be noted that, the present invention accidentally isolated a new compound h. According to ESI-MS analysis, compound h shall have a chemical formula of $C_{15}H_{16}O_4$ (m/z 260), and according to HREIMS analysis, compound h shall have a chemical formula of $C_{15}H_{16}O_4$ (m/z 260.1042 [M]$^+$; calculation value is 260.1049). compound h has 15 carbon signals, which include 6 aromatic carbon ($\delta_C$=139.8, 139.5, 137.1, 136.2, 127.9, 109.8), 2 acetylenic carbon ($\delta_C$=97.5, 83.5), 2 olefinic carbon ($\delta_C$=127.2, 121.1), 2 methoxyl group ($\delta_C$=60.4, 60.0), 2 methyl carbon ($\delta_C$=23.6, 13.9) and 1 methylene carbon ($\delta_C$=101.4).

Under nuclear magnetic resonance spectroscopy ($^1$H NMR), compound h reflects 2 methoxyl group ($\delta_H$=3.98, s, 3H; 3.87, s, 3H), 1 methylenedioxy proton ($\delta_H$=5.98, s, 2H), 2 vinyl proton ($\delta_H$=5.38, br s, 1H, 5.27, br s, 1H) and 2 methyl proton $\delta_H$=2.27, s, 3H; 2.01, s, 3H). The number of carbons and protons measured through $^{13}C$ and $^1H$ NMR is consistent with the measurement result of HREIMS. Except the number of methoxyl groups and methylenedioxy, the $^{13}C$ and $^1H$ NMR spectrum of compound h is similar to Antrocamphin A. This newly isolated compound h is named as Antrocamphin C.

Antrocamphin C, having a structural formula represented by the following Formula II, is yellow powder, HREIMS m/z 260.1042, [M]$^+$ $C_{15}H_{16}O_4$ (Calculation value of molecular weight is 260.1049). EIMS (70 eV) m/z (relint): 260 (100) [M]$^+$, 245 (28), 161 (17), 146 (7), 128 (6), 117 (6), 116 (8), 115 (14), 104 (14), 103 (11), 91 (10), 77 (10). $^1H$ NMR $\delta$ (600 MH$_z$, CDCl$_3$): 5.94 (2H, s, COCH$_2$OC), 5.38 (1H, br s, H$_b$-4'), 5.27 (1H, br s, H$_a$-4'), 3.98 (3H, s, OCH$_3$-5), 3.87 (3H, s, OCH$_3$-6), 2.27 (3H, s, CH$_3$-3), 2.01 (3H, s, CH$_3$-3'). $^{13}C$ NMR $\delta$ (125 MH$_z$, CDCl$_3$): 139.8 (C-5), 139.5 (C-1), 137.1 (C-2), 136.2 (C-6), 127.9 (C-3), 127.2 (C-3'), 121.1 (C-4'), 109.8 (C-4), 101.4 (COCH$_2$OC), 97.5 (C-2'), 83.5 (C-1'), 60.4 (OCH$_3$-5), 60.0 (OCH$_3$-6), 23.6 (OCH$_3$-3'), 13.9 (CH$_3$-3).

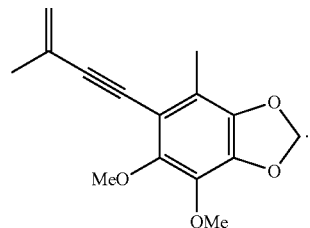

(II)

Embodiment IV: Analyze the Composition of *Antrodia Cinnamomea* Extract Obtained from Embodiment II As mentioned in Embodiment I, based on different sources, culturing time and culturing condition, the present invention used 9 strains for the experiments: AC-3-9, AC-5-9, AC-7-9, AC-9-3, AC-9-6, AC-9-9, AC-9-12, AC-9-9-CC, AC-9-9-CK. In Embodiment II, the present invention analyzed the composition of AC-9-9 *Antrodia Cinnamomea* sporophore extract. In this embodiment, the present invention further analyzed the compositions of the sporophore extract of other experiment strains, in an attempt to find representative physical metabolites.

Use the HPLC method mentioned in Embodiment III to analyze the compositions of AC-3-9, AC-5-9, AC-7-9 *Antrodia Cinnamomea* sporophore extract, and compare with the results of AC-9-9. The comparison is shown in FIG. 1. According to the figure, the types and proportions of the compositions of AC-3-9, AC-7-9, AC-9-9 extracts are very close, with the content of compound i having the highest percentage in the extract. Although the composition of AC-5-9 is slightly different, it also contains the 13 compounds known from the analysis in Embodiment III, with the content of compound g having the highest percentage. The following Table 3 shows the contents of the 13 compounds in AC-3-9, AC-5-9, AC-7-9 and AC-9-9 extracts.

TABLE 3

Compositions of AC-3-9, AC-5-9, AC-7-9 and AC-9-9 extracts

| | Content (mg/each g of dry sporophores) | | | |
|---|---|---|---|---|
| compound | AC-3-9 | AC-5-9 | AC-7-9 | AC-9-9 |
| a | 1.956 ± 0.154b | 0.191 ± 0.013a | 3.250 ± 0.110c | 4.319 ± 0.587d |
| b | <0.001a | <0.001a | <0.001a | 0.001 ± 0.000b |
| c | 1.265 ± 0.104a | 0.820 ± 0.063a | 0.917 ± 0.015a | 1.537 ± 1.020a |
| d | <0.001a | 0.044 ± 0.005b | 0.083 ± 0.002c | 0.046 ± 0.005d |
| e | 0.013 ± 0.000a | 0.238 ± 0.001d | 0.216 ± 0.001c | 0.081 ± 0.007b |
| f | 3.319 ± 0.304b | 0.072 ± 0.005a | 3.760 ± 0.273c | 3.921 ± 0.162c |
| g | 1.226 ± 0.032a | 7.866 ± 0.224c | 2.816 ± 0.298b | 1.389 ± 0.077a |
| h | 0.772 ± 0.002c | 5.390 ± 0.003d | 0.286 ± 0.002a | 0.426 ± 0.040b |
| i | 3.127 ± 0.408a | 2.889 ± 0.364a | 5.787 ± 0.501b | 3.381 ± 0.364a |
| j | <0.001a | 0.002 ± 0.000b | 0.010 ± 0.002d | 0.006 ± 0.000c |
| k | 0.635 ± 0.051a | 0.767 ± 0.002b | 1.153 ± 0.089d | 0.983 ± 0.059c |
| l | 0.008 ± 0.010a | 0.232 ± 0.021c | 0.225 ± 0.026c | 0.073 ± 0.020b |
| m | 2.402 ± 0.191c | 6.284 ± 0.492d | 1.921 ± 0.220ab | 1.683 ± 1.187a |

The contents of all the ingredients are calculated through standard linear equation, wherein Value y is the area of crest, Value x is density of the analyzed material. In each column, the statistically different values (p < 0.05) are shown by different marks (a, b, c, d).

In addition, use the HPLC method again as Embodiment III to analyze AC-9-3, AC-9-6, AC-9-12 *Antrodia Cinnamomea* sporophore extract, and compare with the results of AC-9-9. The comparison is shown in FIG. 2. From the figure, it is known that, during the process of culturing AC-9 strain on *Cinnamoum Kanehirai* for 3—12 months, the compositions of the sporophores of *Antrodia Cinnamomea* will differ along with the time change. The compositions of AC-9-3 sporophores are simple, only having two crests representing compound g and compound m. Along with the time increase, the compositions of the sporophores of *Antrodia Cinnamomea* become more and more diversified, and tend to the 13 physical metabolites obtained from the analysis in Embodiment III. This experimental result tells us that the emergence of stable contents of the 13 physical metabolites can represent the maturity of *Antrodia Cinnamomea*. The following Table 4 shows the contents of the 13 compounds contained in AC-9-3, AC-9-6, AC-9-9 and AC-9-12 extracts.

TABLE 4

Compositions of AC-9-3, AC-9-6, AC-9-9 and AC-9-12 extracts

| | Content (mg/each g of dry sporophores) | | | |
|---|---|---|---|---|
| compound | AC-9-3 | AC-9-6 | AC-9-9 | AC-9-12 |
| a | <0.001a | 0.322 ± 0.004a | 4.319 ± 0.587d | 4.329 ± 0.207b |
| b | <0.001a | 0.005 ± 0.001c | 0.001 ± 0.000b | 0.001 ± 0.000b |
| c | <0.001a | 2.059 ± 0.080b | 1.537 ± 1.020a | 0.362 ± 0.071a |
| d | <0.001a | 0.166 ± 0.004c | 0.046 ± 0.005d | 0.003 ± 0.002a |
| e | 0.841 ± 0.001d | 0.530 ± 0.004c | 0.081 ± 0.007b | 0.025 ± 0.001a |
| f | <0.001a | 0.911 ± 0.020b | 3.921 ± 0.162c | 4.807 ± 0.226d |
| g | 10.312 ± 0.511c | 6.234 ± 0.302b | 1.389 ± 0.077a | 1.135 ± 0.025a |
| h | <0.001a | 1874 ± 0.016d | 0.426 ± 0.040b | 0.660 ± 0.001c |
| i | <0.001a | 3.109 ± 0.792b | 3.381 ± 0.364a | 2.598 ± 0.497b |
| j | 0.011 ± 0.001b | 0.121 ± 0.001d | 0.006 ± 0.000c | 0.014 ± 0.000c |

TABLE 4-continued

Compositions of AC-9-3, AC-9-6, AC-9-9 and AC-9-12 extracts

| | Content (mg/each g of dry sporophores) | | | |
|---|---|---|---|---|
| compound | AC-9-3 | AC-9-6 | AC-9-9 | AC-9-12 |
| k | 0.103 ± 0.002a | 0.451 ± 0.000b | 0.983 ± 0.059c | 0.068 ± 0.022a |
| l | 0.032 ± 0.042a | 1.041 ± 0.106b | 0.073 ± 0.020b | 0.058 ± 0.010a |
| m | 18.058 ± 1.351c | 5.821 ± 0.740b | 1.683 ± 1.187a | 0.887 ± 0.128a |

The contents of all the ingredients are calculated through standard linear equation, wherein Value y is the area of crest, Value x is density of the analyzed material. In each column, the statistically different values (p < 0.05) are shown by different marks (a, b, c, d).

From the result of this embodiment, it is known that the 13 compounds obtained from the analysis in Embodiment III are representative physical metabolites during the maturing process of *Antrodia Cinnamomea*. These compounds have similar contents in different strains. More importantly, most of them have great potential medicinal value. Hence, by analyzing the contents of these 13 compounds in the *Antrodia Cinnamomea* extract, the quality of the *Antrodia Cinnamomea* extract can be quickly determined.

Embodiment V: Analyze the Medicinal Value of the Compounds Isolated from Embodiment III In the traditional medical and academic circles in Taiwan, there have been a lot of studies on the medicinal value of *Antrodia Cinnamomea*. This embodiment will analyze the anti-inflammation effectiveness of the compounds obtained from Embodiment II.

This embodiment uses an analytical method to induce the macrophage of an inflaming mouse, with combination of Greiss reaction, to measure nitrites so as to indirectly measure the output of nitrogen monoxide (NO). As NO is a significant factor in the inflaming reaction, the output of NO can be used to evaluate the degree of inflaming reaction.

In brief, culture mouse macrophage (RAW 264.7 cell) pre-cultured in a 75 cm$^2$ culture dish in a 96 well plate at a density of $2\times10^5$ cells/well. The culture solution used is DMEM with 10% FBS, 100 units/mL penicillin and 100 μg/mL streptomycin. The culturing environment is 37° C. and 5% $CO_2$ cell incubator. Let the normally attaching cells pass or not pass the LPS (1 μg/mL) processing with addition or no addition of the compounds obtained from Embodiment II. Then, use Greiss reaction to measure the concentration of nitrites in the upper clarified liquid of the culture solution after culturing the cells.

The experimental results are shown in FIG. 3, wherein, the ability of each compound to inhibit production of NO is shown through the method of $IC_{50}$. $IC_{50}$ represents 50% of the inhibiting concentration, i.e., 50% of the free radicals are captured by the tested samples. From the data in the figure, it is known that the compounds obtained from Embodiment II all manifest an effect of inhibiting production of NO, i.e., an anti-inflammation effect. Except that the $IC_{50}$ of compounds b, e, g, m are higher than 20 μg/mL (about 20~35m/mL), the $IC_{50}$ of other compounds are all lower than 20 μg/mL. The newly isolated compound h and its structural analog Antrocamphin A both manifest excellent anti-inflammation ability.

Moreover, an MTT trial is conducted to test the biotoxity of each compound. The experiment result shows that, under a dosage of 5~40 μg/mL, none of the compounds is biologically poisonous.

DETAILED DESCRIPTION OF THE INVENTION

Figure 1:
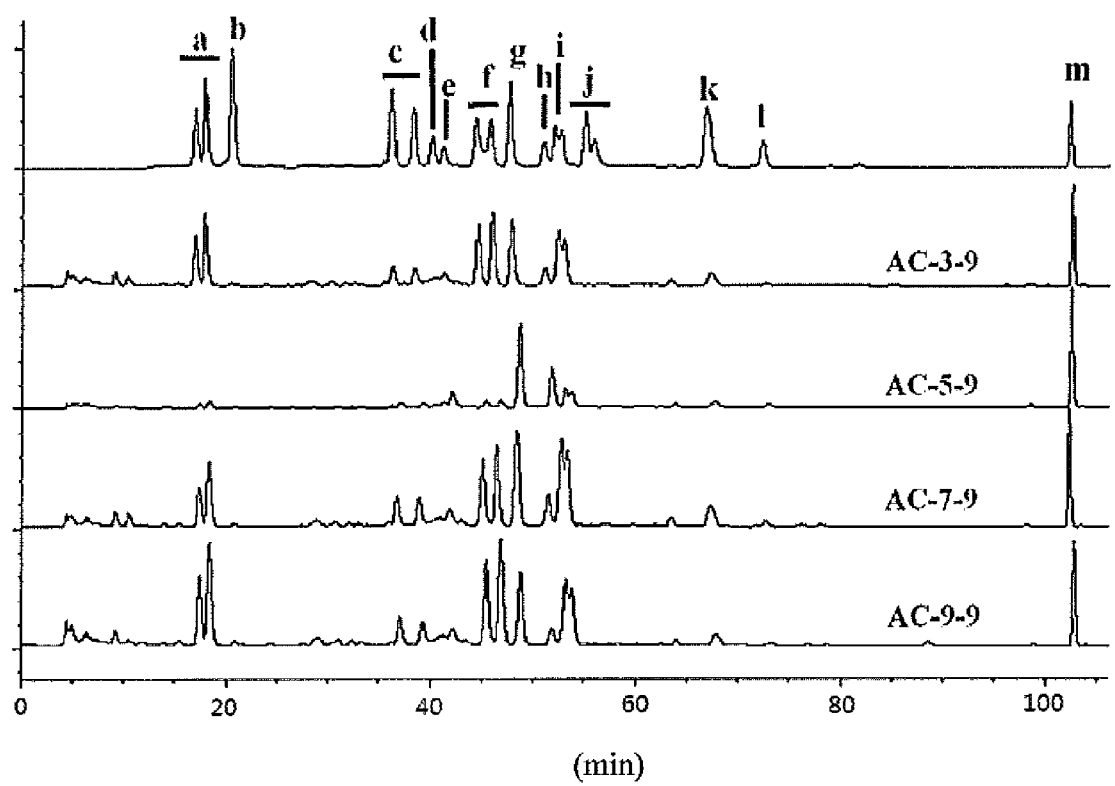
FIG. 1 shows the HPLC analysis atlas of the extracts of AC-3-9, AC-5-9, AC-7-9 and AC-9-9 of the present invention.
Figure 2:
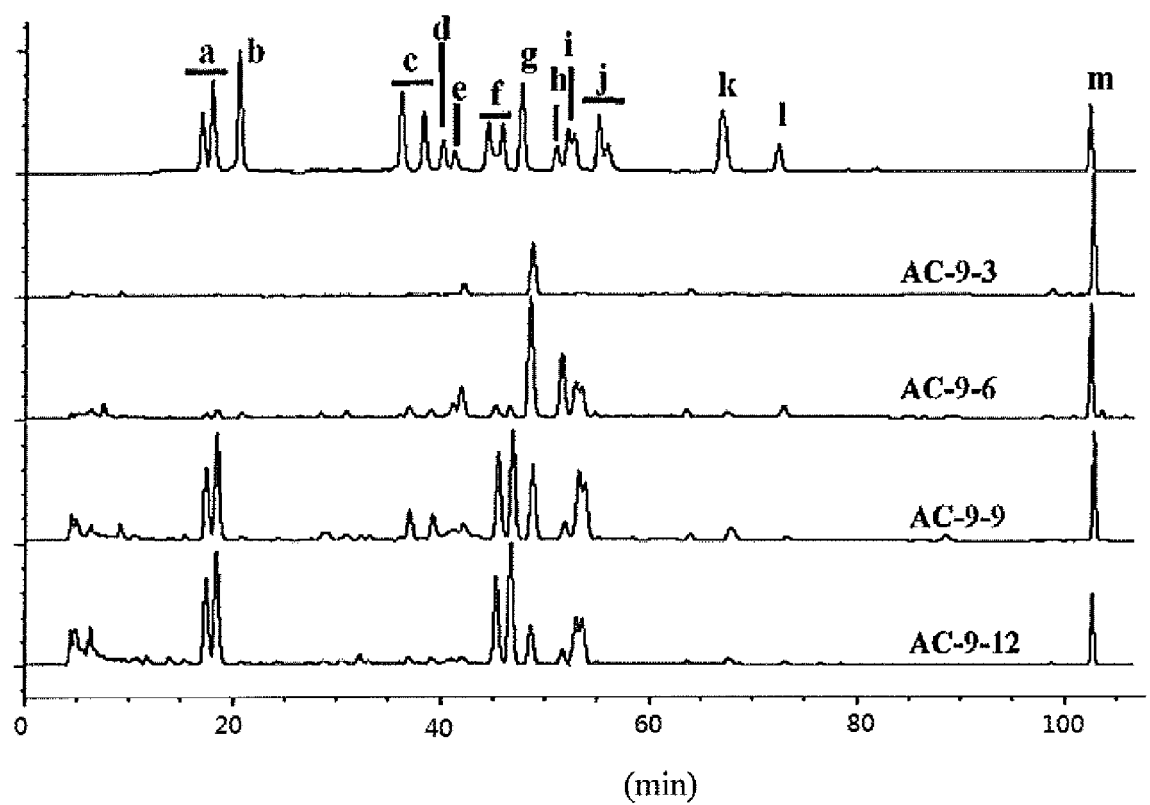
FIG. 2 shows the HPLC analysis atlas of the extract of AC-9-3, AC-9-6, AC-9-9 and AC-9-12 of the present invention.
Figure 3:
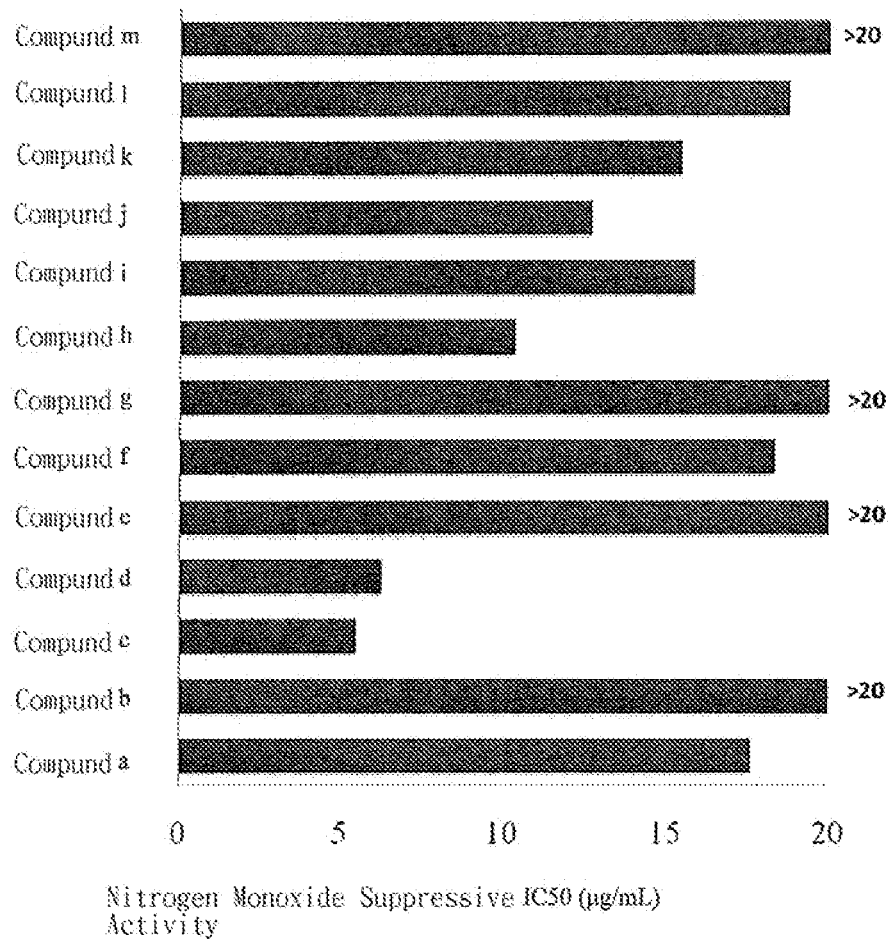
FIG. 3 depicts the nitrogen monoxide suppressive activity of the compound obtained from Embodiment III of the present invention.

Therefore, one objective of the present invention is to provide a new compound, which is extracted from *Antrodia Cinnamomea*, and which has medicinal value.

Another objective of the present invention is to provide a pharmaceutical composition, which contains active ingredients extracted from *Antrodia Cinnamomea*, and which can fulfill the purpose of properly using the property of *Antrodia Cinnamomea*.

A further objective of the present invention is to provide a method to evaluate the quality of *Antrodia Cinnamomea*, which can determine the representative physical metabolite based on the studies on the metabolism during the growing and maturing processes of *Antrodia Cinnamomea*, and consequently determine the growth quality and state of *Antrodia Cinnamomea*.

To fulfill the above purposes, the present invention provides a polyacetylene compound, which has a structural formula represented by the following Formula (I):

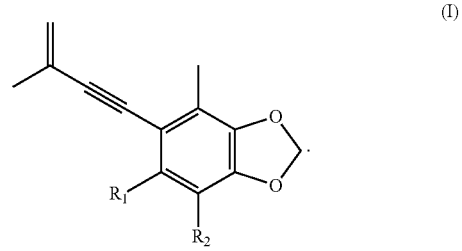

(I)

Preferably, the above R1 and R2 is identical or different alkoxy.

Preferably, the above alkoxy is alkoxy of C1~C4.

Preferably, the above polyacetylene compound has a structural formula represented by the following Formula (II):

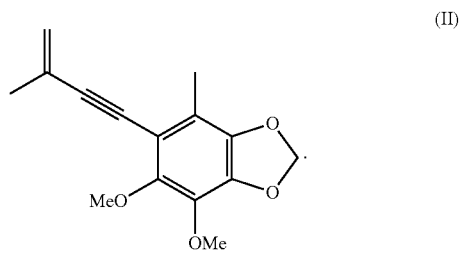 [SMILES: C=C(C)C#Cc1c(C)c2c(c(OC)c1OC)OCO2 ; "."]

(II)

The present invention further provides an *Antrodia Cinnamomea* extract, which contains a polyacetylene compound with a structural formula represented by the following Formula (II):

(II)

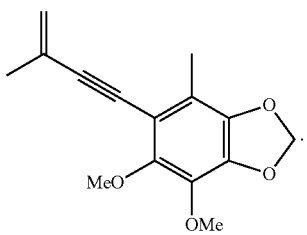

Preferably, the above extract is extracted from the sporophores of *Antrodia Cinnamomea*.

The present invention further provides a pharmaceutical composition, which contains: an effective amount of active ingredients; and medically acceptable carriers; wherein, said active ingredients is polyacetylenes or *Antrodia Cinnamomea* extract.

Preferably, the above pharmaceutical composition contains 5~95 wt % of the above active ingredients; and 5~95 wt % of the above medically acceptable carrier.

Preferably, the above pharmaceutical composition is used to inhibit inflammation.

Preferably, the above pharmaceutical composition is used to inhibit production of nitric oxide.

Preferably, the above medically acceptable carrier is lactose, starch, cellulose derivatives, magnesium stearate, steric acid, water, appropriate oils, normal saline solution, water solution of dextrose or any combination of the above.

Preferably, the above pharmaceutical composition is in dosage forms of capsule, pastille, dispersant, liquid, suspension or injection.

The present invention further provides a method to evaluate the quality of *Antrodia Cinnamomea*, which includes the following steps: a. Obtain dry sporophores of *Antrodia Cinnamomea*; b. Obtain alcohol extract of the above sporophores of *Antrodia Cinnamomea*; and c. Analyze the contents of triterpenoids, polyacetylenes and benzenoids in the above alcohol extract to determine the quality of *Antrodia Cinnamomea*; wherein the above polyacetylenes contain a compound having a structural formula represented by the following Formula (II):

(II)

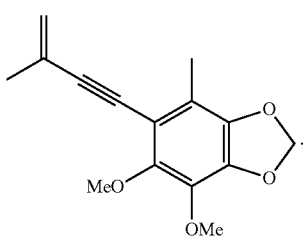

Preferably, the above triterpenoids contain *Antrodia Cinnamomea* Acid K, *Antrodia Cinnamomea* Acid C, *Antrodia Cinnamomea* Acid H, dehydrosulfurenic acid, *Antrodia Cinnamomea* Acid B, *Antrodia Cinnamomea* Acid G, *Antrodia Cinnamomea* Acid A, 15-Acetyl-dehydrosulfurenic acid, dehydroeburicoic acid.

Preferably, the above polyacetylenes further contain Antrocamphin A.

Preferably, the above benzenoids contain 1,4-dimethoxy-2,3-methylenedioxy-5-toluene and 2,2',5,5'-tetramethoxy-3,4,3',4'-bimethylenedioxy-6,6'-dimethyl biphenyl.

Preferably, the above Step b includes mixing the dry sporophores of *Antrodia Cinnamomea* with alcohol, and an extraction time of 60~120 min.

Preferably, the above analytical method is HPLC method.

Preferably, the fixed phase of said HPLC method is Luna C18 column, and the mobile phase is a mixture of water, methyl and acetonitrile.

In summary, the present invention is related to the polyacetylenes extracted from *Antrodia Cinnamomea*, the extract containing the above, and the pharmaceutical composition with the above compound or extract as its active ingredients. The present invention discovered that the polyacetylenes has a function of inhibiting the production of nitric oxide, and therefore an anti-inflammation effect. On the other hand, the present invention determined the representative physical metabolite based on the studies on the metabolism during the growing and maturing processes of *Antrodia Cinnamomea*, and further established a method to evaluate the quality of *Antrodia Cinnamomea* by analyzing such representative physical metabolite.

The invention claimed is:

1. A polyacetylenes, having a structural formula represented by the following Formula (I):

(I)

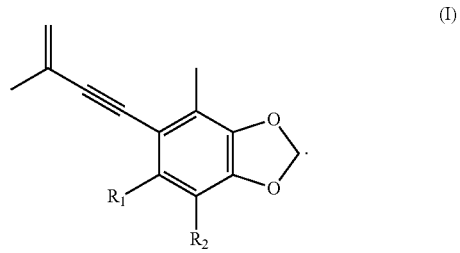

wherein R1 and R2 is identical or different alkoxy.

2. The polyacetylenes as claimed in claim 1, wherein said alkoxy is alkoxy of C1-C4.

3. The polyacetylenes as claimed in claim 1, which has a structural formula represented by the following Formula (II):

(II)

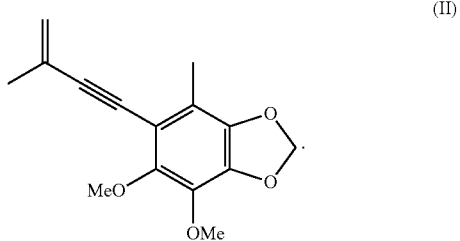 [SMILES: C=C(C)C#Cc1c(C)c2c(c(OC)c1OC)OCO2 ; "."]

4. An *Antrodia Cinnamomea* extract comprising polyacetylenes with a structural formula represented by the following Formula (II):

(II)

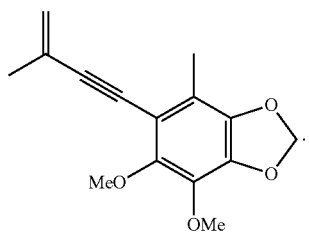

5. A pharmaceutical composition, which contains: an effective amount of active ingredients; and medically acceptable carrier; wherein, said active ingredients is polyacetylenes as claimed in claim 1 or *Antrodia Cinnamomea* extract as claimed in claim 4.

6. The pharmaceutical composition as claimed in claim 5, which contains 0.1-95 wt % of said active ingredients; and 0.1-95 wt % of said medically acceptable carrier.

7. The pharmaceutical composition as claimed in claim 5, wherein the medically acceptable carrier is lactose, starch, magnesium stearate, steric acid, water, appropriate oils, normal saline solution, water solution of dextrose or mixture thereof.

8. The pharmaceutical composition as claimed in claim 5, which is in dosage forms of capsule, pastille, dispersant, liquid, suspension or injection.

9. A method to evaluate the quality of *Antrodia cinnamomea*, comprising the following steps:
   a. obtain dry sporophores of *Antrodia Cinnamomea*;
   b. obtain methanol extract of the above sporophores of *Antrodia Cinnamomea*; and
   c. analyze the contents of triterpenoids, polyacetylenes and benzenoids in the above alcohol extract to determine the quality of *Antrodia Cinnamomea*;

wherein said polyacetylenes contain a compound with structural formula represented by the following Formula (II):

(II)

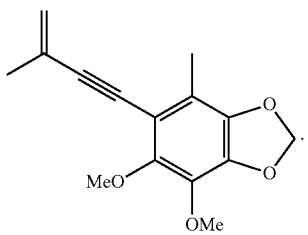

10. The method to evaluate the quality of *Antrodia Cinnamomea* as claimed in claim 9, wherein said triterpenoids contain *Antrodia Cinnamomea* Acid K, *Antrodia Cinnamomea* Acid C, *Antrodia Cinnamomea* Acid H, dehydrosulfurenic acid, *Antrodia Cinnamomea* Acid B, *Antrodia Cinnamomea* Acid G, *Antrodia Cinnamomea* Acid A, 15-Acetyl-dehydrosulfurenic acid, dehydroeburicoic acid.

11. The method to evaluate the quality of *Antrodia Cinnamomea* as claimed in claim 9, wherein said polyacetylenes further contain Antrocamphin A.

12. The method to evaluate the quality of *Antrodia Cinnamomea* as claimed in claim 9, wherein said benzenoids contain 1,4-dimethoxy-2,3-methylenedioxy-5-toluene and 2,2'5,5'-tetramethoxy-3,4,3',4'-bimethylenedioxy-6,6'-dimethylbiphenyl.

13. The method to evaluate the quality of *Antrodia Cinnamomea* as claimed in claim 9, wherein said Step b has an extraction time of 60~120 min.

* * * * *